United States Patent [19]

Auger et al.

[11] Patent Number: 5,618,718

[45] Date of Patent: Apr. 8, 1997

[54] PRODUCTION OF A CONTRACTILE SMOOTH MUSCLE

[75] Inventors: François A. Auger; Nicolas L'Heureux; Lucie Germain, all of Quebec, Canada

[73] Assignee: Université Laval, Quebec, Canada

[21] Appl. No.: 368,205

[22] Filed: Dec. 30, 1994

[51] Int. Cl.$^6$ .............................. C12N 5/00; C12N 5/08; A61F 2/08

[52] U.S. Cl. ........................ 435/366; 435/371; 435/373; 435/378; 435/379; 435/395; 424/422

[58] Field of Search ........................... 435/240.2, 240.23, 435/240.241, 240.242; 604/14, 66; 424/422

[56] References Cited

U.S. PATENT DOCUMENTS

| | | | |
|---|---|---|---|
| 4,416,028 | 11/1983 | Eriksson et al. | 3/1.4 |
| 4,546,500 | 10/1985 | Bell | 623/1 |
| 4,787,900 | 11/1988 | Yannas | 623/1 |
| 4,804,382 | 2/1989 | Turina et al. | 623/1 |
| 4,902,289 | 2/1990 | Yannas | 623/1 |
| 4,963,489 | 10/1990 | Naughton et al. | 435/210.1 |
| 4,997,443 | 3/1991 | Walthall et al. | 623/11 |
| 5,230,693 | 7/1993 | Williams et al. | 600/36 |
| 5,254,471 | 10/1993 | Mori et al. | 435/240.243 |
| 5,266,480 | 11/1993 | Naughton et al. | 435/240.243 |
| 5,443,950 | 8/1995 | Naughton et al. | 435/1 |

FOREIGN PATENT DOCUMENTS

| | | |
|---|---|---|
| 1291433 | 10/1991 | Canada . |
| 0175286 | 3/1986 | European Pat. Off. . |
| 278817 | 8/1988 | European Pat. Off. . |
| 0282746 | 9/1988 | European Pat. Off. . |
| 0387975 | 9/1990 | European Pat. Off. . |
| 62-48376 | 3/1987 | Japan . |
| 4-303451 | 10/1992 | Japan . |
| WO81/01416 | 5/1981 | WIPO . |
| WO90/14417 | 11/1990 | WIPO . |

OTHER PUBLICATIONS

Stiemer, B. et al., Histology and Histopathology, vol. 8(1), pp. 63–72. Jan. 1993.

Ueda, T., J. Tokyo Women's Med. Coll., vol. 57(12), pp. 1624–1635. Dec. 1987.

Leushner, J.R.A. "Biochem. Cell. Biol." vol. 65, 1987, pp. 595–601.

Leushner, JRA et al., "Can. J. Biochem," vol. 63, 1985, pp. 1176–1182.

Kockx, M. M. et al., "Histopathology", vol. 25, #4, Oct. 1994, pp. 365–371.

Goldfischer, S. et al. "Fed. Amer. Soc. for Exp. Biol," 66th Annual Meeting, 1982, abs #998, p. 440.

Holderbaum, D. et al. "J. Cell Biol," vol. 103 (#5, part 2), 1986, p. 99a, abs. #372.

Hwa, J. J. et al., "FASEB Journal," vol. 9, #3, Mar. 1995, p. A412, abs. #2389.

*Primary Examiner*—David M. Naff
*Assistant Examiner*—Kristin Larson
*Attorney, Agent, or Firm*—McAulay Fisher Nissen Goldberg & Kiel, LLP

[57] ABSTRACT

A contractile smooth muscle cell construct and a method for preparing the smooth muscle cell construct are described. The smooth muscle cell construct is comprised of (i) smooth muscle cells that have been cultured in vitro under conditions to allow the formation of a sheet of smooth muscle cells and (ii) an endogenous fibrous matrix formed by the smooth muscle cells, wherein the smooth muscle cell construct retains the ability to contract in response to vasoactive agonists. The smooth muscle cell construct may be prepared in planar or tubular form and can be used to study or evaluate the contractile responses of smooth muscle cells.

9 Claims, 2 Drawing Sheets

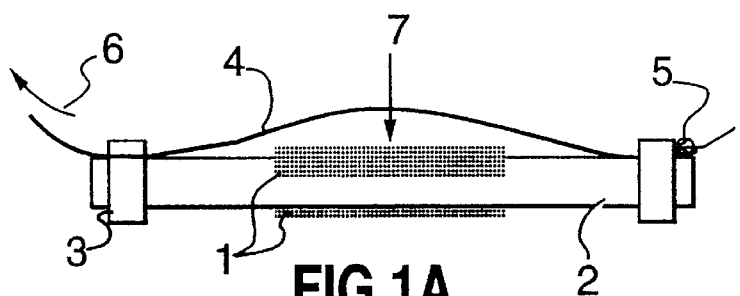 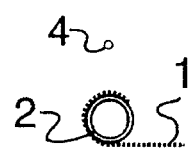
FIG.1A      FIG.1B
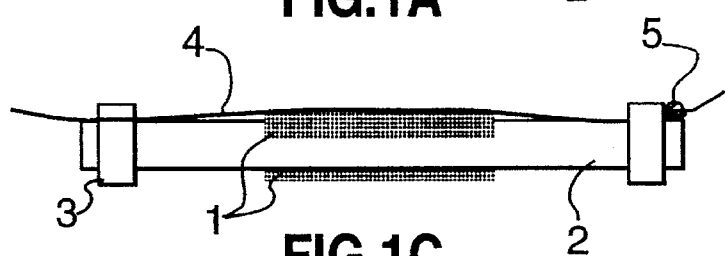 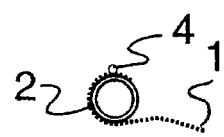
FIG.1C      FIG.1D
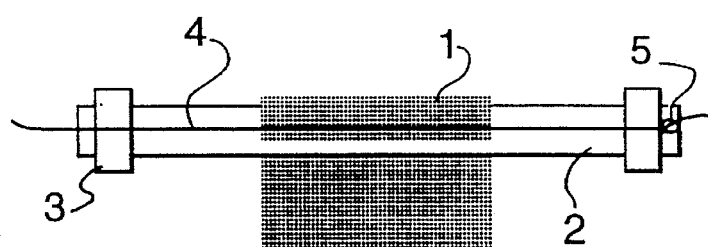 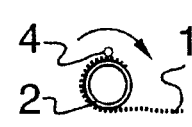
FIG.1E      FIG.1F
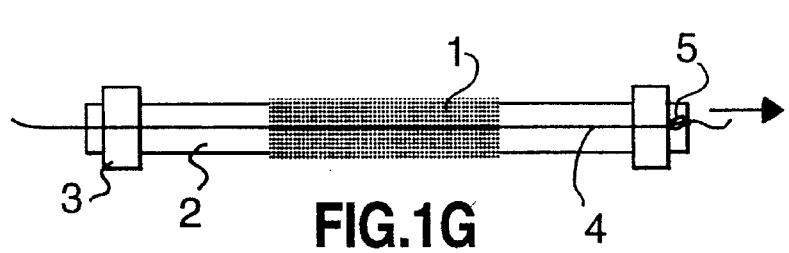 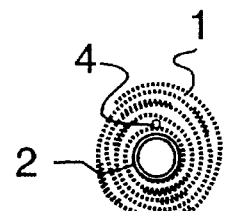
FIG.1G      FIG.1H
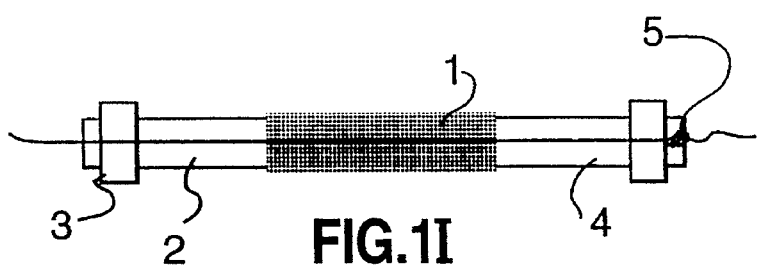 
FIG.1I      FIG.1J

PRODUCTION OF A CONTRACTILE SMOOTH MUSCLE

FIELD OF THE INVENTION

This invention is in the field of tissue engineering. In particular the invention relates to the production, in vitro, of a three-dimensional preparation of a smooth muscle cell construct which contracts as a whole tissue in response to physiological stimuli. This smooth muscle construct has numerous applications including pharmacological testing, organ modeling for research purposes and vascular prosthesis development.

BACKGROUND OF THE INVENTION

When vascular smooth muscle cells are cultured, in vitro, they lose their contractile response to vasocontractile substances. This phenotypic modulation greatly limits vascular medical research to animal and animal organ experimentation, especially in such fields as hypertension. While some indirect information can be obtained from non-contracting smooth muscle cell cultures, results of such experiments must be carefully interpreted. Furthermore, even though it is possible to obtain contractile smooth muscle cells in vitro, if they are freshly isolated (primoculture), this technique is limited by the number of cells obtainable and clinically available human tissue.

The various methods described, up until now, to evaluate contractile responses of smooth muscle cell cultures have three common and serious weaknesses: 1) the cells are on non-physiological substrata, 2) quantitative evaluation of contraction forces are not possible, and 3) quantitative assessment of contraction is made on a "single-cell basis" (although numerous cells can be studied concurrently) and therefore, does not necessarily provide information on a "tissue basis" response. Recently, some two-dimensional sub-cultures of non-vascular animal smooth muscle cells have shown limited contractile responses to appropriate stimulants. Nevertheless, human sub-cultured smooth muscle cell contraction in particular cells of vascular origin, has yet to be demonstrated.

Consequently there is a need to develop a smooth muscle cell construct that can be useful as an in vitro replica of smooth muscle responses in vivo.

SUMMARY OF THE INVENTION

The present invention provides a contractile smooth muscle cell construct comprised of (i) smooth muscle cells that have been cultured in vitro under conditions to allow the formation of a sheet of smooth muscle cells and (ii) an endogenous fibrous matrix formed by the smooth muscle cells; wherein the smooth muscle cell construct retains the ability to contract in response to vasoactive agonists. In one embodiment the smooth muscle cell construct may be prepared in tubular form. This smooth muscle cell construct is representative of the basic structure of a vascular media, the contractile element of a blood vessel, and shows contractile responses to normal vasocontractile agonists. Thus, this invention allows the quantitative investigation of isometric contractile forces generated by pure populations of cultured, or sub-cultured, human vascular smooth muscle cells, in a physiological environment and on a "tissue basis". This tissue equivalent, contracting as a whole, is an actively vasoresponsive structure similar to its physiological counterpart: the media.

The present invention also provides a method of producing a contractile smooth muscle cell construct said method comprising:

(a) culturing the smooth muscle cells in a culture vessel with a culture medium that enhances the synthesis of a fibrous matrix by the cells;

(b) maintaining the cells in culture until the cells adhere to the culture vessel, become confluent and form a cell sheet; and (c) allowing the cell sheet to spontaneously detach or detaching the cell sheet from a culture vessel. The cell sheet can be detached using various means such as enzymatic or mechanical detachment.

The method can also include an additional step (d) wherein said cell sheet is rolled around a tubular support to produce a tubular cell construct.

BRIEF DESCRIPTION OF THE DRAWINGS

FIG. 1A–J is a schematic diagram showing the preparation of a tubular living tissue construct according to the method of the present invention.

DETAILED DESCRIPTION OF THE INVENTION

Figure 2A:
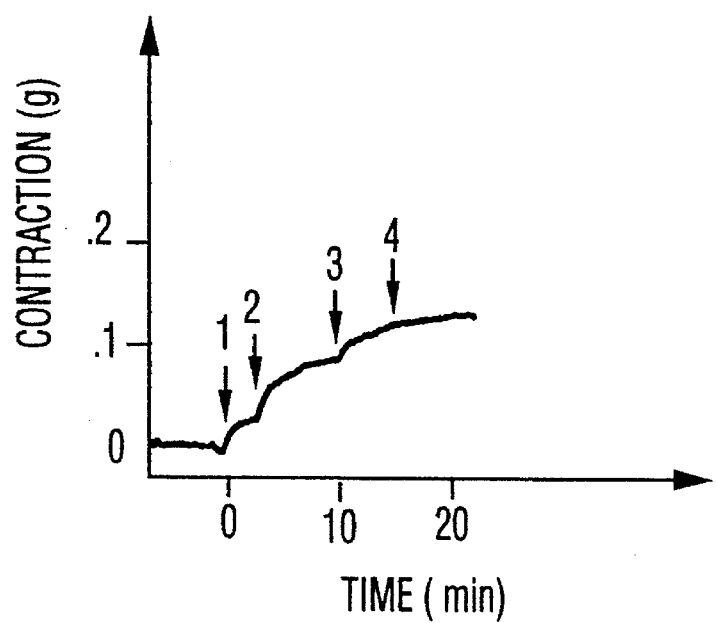
FIG. 2A is a dose-response curve showing the contraction of a living tissue construct in response to varying concentrations of serotonin.

It has been determined that cells of mesenchymal origin (such as smooth muscle cells and fibroblasts) will grow as a multilayer of cells intertwined In an extracellular matrix (e.g. collagen) synthesized by the cells themselves. When these cells are cultured in the presence of ascorbic acid, they reach confluence faster and the proportion of the collagenous component of the above-mentioned cultures increases drastically. If these cells are maintained in culture several days past confluence, cells and matrix will detach as a whole from the culture substratum, thus creating a sheet of living cells in a collagenous matrix of endogenous origin.

The spontaneous detachment of such living sheet is achieved by enhancing collagen (or other matrix protein) synthesis or assembly in the cell culture. Detachment may also be induced by lowering the strength of the cell to substratum junction, for example by lowering substratum adhesiveness, by using proteolytic enzymes or by using mechanical force.

Once a sheet of living tissue is obtained, it can be rolled on the outer surface of a tubular support of varying diameter to give it a tubular form. If the sheet is held in place while rolled up for a few hours in suitable cell culture conditions, it will adhere to itself relatively firmly and will stay in its tubular form, around its tubular support. The tubular tissue hence created may be kept in culture conditions for extended periods of time and submitted to various culture conditions to influence its ongoing development (ascorbic acid, serum, mitogens, etc.)

At the end of its maturation period, the tubular tissue can be slid off its tubular support to provide the basic scaffold for the construction of a more complex tissue culture system. For example, endothelial cells can be seeded on the inner surface of a tubular tissue made of smooth muscle cells, hence producing a basic blood vessel construct or prosthesis.

Such a tubular tissue prosthesis can be useful in tissue transplantation as it can be made from the cells of the graft recipient, thus circumventing immunological rejection of the prosthesis. Furthermore, the tubular tissue can be rolled up in a similarly produced sheet to obtain a two layer tubular lining tissue construct. Cells which form the second layer can be of identical nature to the cells of the first layer to obtain a thicker tissue, or of different origin (such as fibroblasts) to create a two cell type living organ equivalent in order, for example, to study cell-cell interactions.

To study smooth muscle cell contraction, the tubular tissue, made of smooth muscle cells, is slid off its tubular support and cut in annular sections of desired width. Alternatively, the annular sections may be cut before the tubular tissue is slid off the support. Such an annular section can be mounted on an isometric force transducer, whilst in an organ culture bath, and submitted to a basal tension. Stimulations can be carried on by injecting vasoactive substances in the bath and recording the contractile response through the transducer output. This technique is well established and this invention can be a substitute for animal blood vessels which are normally used as contractile tissue.

EXAMPLE 1: Preparation of Contractile Smooth Muscle Cell Sheet

The following example describes one method for preparing a contractile tubular tissue made of smooth muscle cells according to the present invention. It is not intended to limit the scope of this invention to one particular shape, cell origin or age, time frame, component concentration or culture condition. One skilled in the art can readily appreciate that various modifications can be made to the method without departing from the scope and spirit of the invention.

Typically, 750,000 viable sub-cultured human smooth muscle cells (passages 3–7) are seeded in a standard 75 cm$^2$ culture dish for a final seeding density of $10^4$ cells/cm$^2$. Cells are fed with 20 ml of culture medium (3:1 mixture of Dulbecco's Modification of Eagle's Medium and Ham's F12 Modified Medium, 10% Fetal Clone II from Hyclone, 100 U/ml of penicillin G and 25 ug/ml of gentamicin). The culture medium is changed every day. A freshly prepared solution of ascorbic acid is added every day to the culture medium at a final concentration of 100 ug/ml. Cells are kept in a humidified atmosphere (92% air and 8% $CO_2$).

Under the above-mentioned culture conditions, the cells will adhere to the culture surface and proliferate until the entire culture surface is covered with cells (confluence). If the culture conditions are maintained, the cells will grow as a multilayer of cells and endogenous fibrous material. If the culture is prolonged for several additional days, this fibrous tissue will show signs of detachment from the culture substratum and will spontaneously completely detach itself, as a whole, from the substratum. Omitting the ascorbic acid may lead to a longer culture period before detachment and will not produce a cohesive single sheet but rather numerous irregular masses of agglomerated cells. The complete process of spontaneous tissue detachment is a swift and sudden process and can undergo completion in as little as 15 minutes. The resulting free-floating sheet of living tissue must be kept unfolded until the following stage of fabrication since it will readily and irreversibly agglutinate. It is also possible to induce the detachment of the forming sheet, for example in order to control the time of detachment. One possibility is to use a rubber policeman to detach the sheet from the culture surface when signs of detachment are apparent. However, this method must be very carefully performed as it can cause holes in the sheet.

Although this sheet can be used for numerous applications in its planar form, a tubular form will facilitate some other applications. In particular, the tubular form is valuable for experiments relating to vascular physiology and pharmacology. In order to give a cylindrical form to the sheet of tissue the inventors have designed a tubular support as shown schematically in FIGS. 1A through J. Referring to FIG. 1A, the tubular support (2) is equipped with a thread (4) which can be set longitudinally to the external surface of the tubular support. To ensure that the thread is closely laid to the surface of the tubular support, tension is provided by two elastic rings (3) positioned outside at both ends of the tubular support. Typically, a polypropylene thread is secured under a silicone elastomer ring, by means of a stop notch (5), while the other end of the thread is slid under the silicone ring (3) at the other end of the tube.

To roll the living sheet, one edge of the sheet (1) is placed between the tubular support and the thread. The thread (4) is then pulled along the arrow (6) in order to squeeze (7) one edge of the sheet between the thread and the external surface of the tubular support as shown in FIG. 1A. A minimal amount of the sheet should cross over the thread although it is important that all the edges be secured as shown in FIG. 1C. While rolling the living sheet, limited force can be applied to the farther edge of the sheet in order to stretch it to various degrees as shown in FIG. 1E. If the sheet has been mechanically detached, it is useful to leave one of its extremities attached to the culture surface in order to provide such a stretching force upon the rolling of the living sheet. When the sheet is completely rolled up, the thread is slid off by pulling in the direction of the arrow as shown in FIG. 1G. The sheet is then resecured with the thread to prevent unrolling of the sheet as shown in FIG. 1I. Thereafter, the tubular living tissue can be cultured for several weeks, with ascorbic acid, to allow further maturation of the tissue. The thread may be removed 1–2 days later.

The tubular support can be made of various materials. It is usually made of inert matter, such as styrene, to facilitate the removal of the tissue at the end of the maturation period. However, it can also be made of stainless steel, collagen, polytetrafluoroethylene or bioactive or biodegradable materials. It is preferable to use a tube made of a material which can be readily cleaned and sterilized. The outer diameter of the tube will establish the final diameter of the lumen of the tubular living tissue produced (2–8 mm). The thread can be easily replaced following each use. Plastic type thread can also be used if it is cleaned after each use.

Figure 2B:
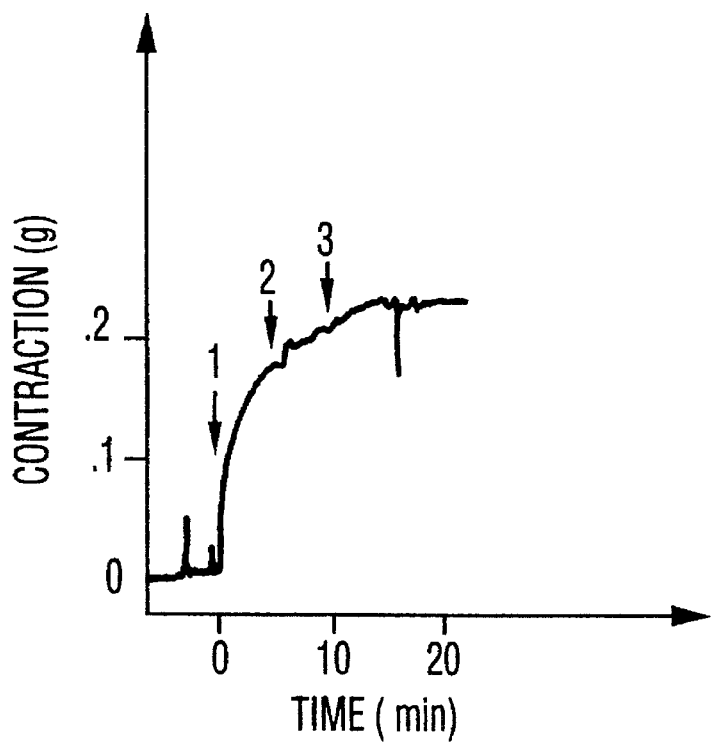
FIG. 2B is a dose-response curve showing the contraction of a living tissue construct in response to varying concentrations of histamine.

After 3 to 4 weeks in the above-mentioned culture conditions the tubular tissue, which is the equivalent of a vascular media, can be slid off its tubular support and cut into annular sections of 2 to 5 mm. These annular sections can be used to test the contraction of smooth muscles in vitro. The annular sections prepared according to the present invention have been tested with two physiological vasoactive substances, namely serotonin and histamine. FIGS. 2A and 2B show the contraction response of annular sections when stimulated with varying concentrations of serotonin (FIG. 2A) and histamine (FIG. 2B). In FIG. 2A, the points (1), (2), (3), and (4) represent stimulation with 30 ng/ml, 100 ng/ml, 300 ng/ml and 1000 ng/ml serotonin, respectively. In FIG. 2B, the points (1), (2), and (3) represent stimulation with $10^{-5}$M, $3\times10^{-5}$M and $10^{-4}$M histamine, respectively. These results are comparable to those obtained using human or animal blood vessel thus demonstrating that the tissue equivalents prepared according to the present invention are useful models of living tissues.

Those knowledgeable in the field of tissue and cell culture will be able to construct equivalent structures, with only the available material in a cell culture laboratory, which can be used for specific applications by simply replacing a particular component or technique by a similar component or technique which will produce the same general effect. Such equivalents are intended to be included in the scope of this invention.

What we claim as our invention is:

1. A contractile smooth muscle cell construct comprising:
   i) sub-cultured human smooth muscle cells that have been cultured in vitro under conditions to allow the formation of a sheet of smooth muscle cells; and
   ii) an endogenous fibrous matrix formed by the smooth muscle cells; wherein the smooth muscle cell construct retains the ability to contract in response to vasoactive agonists.

2. A contractile smooth muscle cell construct according to claim 1 wherein said smooth muscle cell construct is in tubular form.

3. A method for producing the contractile smooth muscle cell construct of claim 1 which comprises:
   a) culturing sub-cultured human smooth muscle cells in a culture vessel with a culture medium that promotes the synthesis of a fibrous matrix by the cells;
   b) maintaining the cells in culture until the cells adhere to the culture vessel, become confluent and the cells and the matrix form a sheet; and
   c) allowing the cell sheet to spontaneously detach or detaching the cell sheet from the culture vessel.

4. The method according to claim 3, wherein said culture medium contains ascorbic acid.

5. The method according to claim 3 further comprising rolling said cell sheet around a tubular support to produce a tubular living tissue construct.

6. The method according to claim 5, further comprising: removing the tubular living tissue construct from the support and maintaining said tubular living tissue construct in culture.

7. The method according to claim 5 further comprising seeding endothelial cells on the inner surface of said tubular living tissue construct.

8. A method of producing a multilayered tubular living tissue construct said method comprising:
   a) creating a tubular living tissue construct according to claim 4;
   b) rolling a second cell sheet around said tubular living tissue construct.

9. The method according to claim 8 wherein said second sheet comprises fibroblasts.

* * * * *

UNITED STATES PATENT AND TRADEMARK OFFICE
CERTIFICATE OF CORRECTION

PATENT NO. : 5,618,718
DATED : April 8, 1997
INVENTOR(S) : Francois A. Auger, et. al.

It is certified that error appears in the above-indentified patent and that said Letters Patent is hereby corrected as shown below:

Column 5, line 12, start new paragraph with "wherein";

Column 6, line 18, change "claim 4" to --claim 5--.

Signed and Sealed this

Eighteenth Day of November 1997

BRUCE LEHMAN

Attest:

Attesting Officer

Commissioner of Patents and Trademarks